(12) United States Patent
Carling et al.

(10) Patent No.: US 6,465,462 B1
(45) Date of Patent: Oct. 15, 2002

(54) SUBSTITUTED TRIAZOLO PYRIDAZINE DERIVATIVES AS INVERSE AGONISTS OF THE GABA$_{A\alpha}$5 RECEPTOR SUBTYPE

(75) Inventors: William Robert Carling; Angus Murray MacLeod, both of Bishops Stortford; Ruth McKernan, Saffron Walden; Austin John Reeve, Great Dunmow; Francine Sternfeld, London; Leslie Joseph Street, Harlow, all of (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/214,882

(22) PCT Filed: Jul. 17, 1997

(86) PCT No.: PCT/GB97/01918

§ 371 (c)(1),
(2), (4) Date: Jan. 14, 1999

(87) PCT Pub. No.: WO98/04560

PCT Pub. Date: Feb. 5, 1998

(30) Foreign Application Priority Data

Jul. 25, 1996 (GB) ............................................. 9615645
Sep. 16, 1996 (GB) ............................................. 9619304

(51) Int. Cl.⁷ ..................... A61K 31/502; C07D 487/04

(52) U.S. Cl. ........................................ 514/248; 544/234
(58) Field of Search ............................ 544/234; 514/248

(56) References Cited

FOREIGN PATENT DOCUMENTS

| EP | 0 085 840 A1 | 8/1983 |
| EP | 0 134 946 A1 | 3/1985 |
| WO | WO 93/04066 | 3/1993 |
| WO | WO 94/26742 | 11/1994 |

OTHER PUBLICATIONS

R.K. McNamara et al., *Psychobiology*, 21:101–108(1993).

*Primary Examiner*—Patricia L. Morris
(74) *Attorney, Agent, or Firm*—J. Eric Thies; Shu M. Lee; Melvin Winokur

(57) ABSTRACT

Compounds of formula (I)

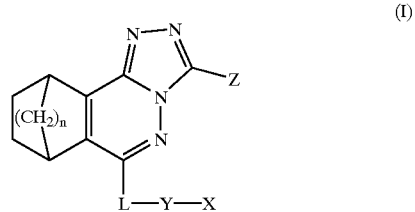

or a pharmaceutically acceptable salt thereof are useful in enhancing cognition.

4 Claims, No Drawings

SUBSTITUTED TRIAZOLO PYRIDAZINE DERIVATIVES AS INVERSE AGONISTS OF THE GABA$_A\alpha$5 RECEPTOR SUBTYPE The present invention relates to a class of substituted triazolopyridazine derivatives and to their use in therapy. More particularly, this invention is concerned with substituted 1,2,4-triazolo[4,3-b]pyridazine derivatives which are ligands for GABA$_A$ $\alpha_5$ receptors and are therefore useful in the therapy where cognition enhancement is required.

Receptors for the major inhibitory neurotransmitter, gamma-aminobutyric acid (GABA), are divided into two main classes: (1) GABA$_A$ receptors which are members of the ligand-gated ion channel superfamily: and (2) GABA$_B$ receptors, which may be members of the G-protein linked receptor superfamily. Since the first cDNAs encoding individual GABA$_A$ receptor subunits were cloned the number of known members of the mammalian family has grown to thirteen (six $\alpha$ subunits, three $\beta$ subunits, three $\gamma$ subunits and one $\delta$ subunit). It may be that further subunits remain to be discovered; however, none has been reported since 1993.

Although knowledge of the diversity of the GABA$_A$ receptor gene family represents a huge step forward in our understanding of this ligand-gated ion channel, insight into the extent of subtype diversity is still at an early stage. It has been indicated that an $\alpha$ subunit a $\beta$ subunit and $\gamma$ subunit constitute the minimum requirement for forming a fully functional GABA$_A$ receptor expressed by transiently transfecting cDNAs into cells. As indicated above, a $\delta$ subunit also exists, but is apparently uncommon in the native receptor.

Studies of receptor size and visualisation by electron microscopy conclude that, like other members of the ligand-gated ion channel family, the native GABA$_A$ receptor exists in pentameric form. The selection of at least one $\alpha$, one $\beta$ and one $\gamma$ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include $\alpha1\beta2\gamma2$, $\alpha2\beta2/3\gamma2$, $\alpha3\beta2/3$, $\alpha2\beta\gamma1$, $\alpha5\beta3\gamma2/3$, $\alpha6\beta\gamma2$, $\alpha6\beta\delta$ and $\alpha4\beta\delta$. Subtype assemblies containing an $\alpha1$ subunit are present in most areas of the brain and account for over 40% of GABA$_A$ receptors in the rat. Subtype assemblies containing $\alpha2$ and $\alpha3$ subunits respectively account for about 25% and 17% of GABA$_A$ receptors in the rat. Subtype assemblies containing an $\alpha5$ subunit are primarily hippocampal and represent about 4% of receptors in the rat.

A characteristic property of some GABA$_A$ receptors is the presence of a number of modulatory sites, of which the most explored is the benzodiazepine (BZ) binding site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the $\alpha1$ subunit in combination with $\beta2$ and $\gamma2$. This is the most abundant GABA$_A$ receptor subtype, representing almost half of all GABA$_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant which makes it clear that they cannot be used as cognition enhancing agents in humans.

However, we have now discovered that it is possible to obtain medicaments which have cognition enhancing effects, but which do not possess proconvulsant effects previously described with benzodiazepine receptor partial or full inverse agonists.

It has now been discovered that use of an $\alpha5$ subtype receptor partial or full inverse agonist which is relatively free of activity at $\alpha_1$ and/or $\alpha_2$ and/or $\alpha_3$ subtype receptor binding sites can be used to provide a medicament which is useful for enhancing cognition but which is not proconvulsant. Inverse agonists at $\alpha_5$ which are not free of activity at $\alpha_1$ and/or $\alpha_2$ and/or $\alpha_3$ but which are selective for $\alpha_5$ can also be used. Inverse agonists which are both selective for $\alpha_5$ and are relatively free of activity at $\alpha_1$, $\alpha_2$ and $\alpha_3$ receptor binding sites are preferred.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolophthalazine ring system with any other functionality nor is there any suggestion that the compounds have any cognition enhancing properties.

The present invention provides a compound of the formula (I):

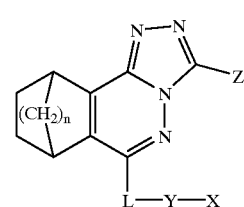

X is: NR$^2$R$^3$; phenyl optionally substituted by one or two groups independently chosen from R$^G$, halogen, CN and OR$^G$, where R$^G$ is C$_{1-6}$alkyl, C$_{2-6}$alkenyl, C$_{2-6}$alkynyl or CF$_3$, or by a methylenedioxy or ethylenedioxy group; or a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2, 3, or 4 nitrogen atoms, the ring being optionally fused to a benzene ring and optionally substituted by one or more groups independently chosen from R$^7$, OR$^7$, OCOR$^7$, NR$^8$R$^9$, NR$^8$COR$^9$, CN and CF$_3$ where R$^7$ is independently as defined for R$^G$, R$^8$ is independently as defined for R$^2$ and R$^9$ is independently as defined for R$^3$, when the 6-membered heteroaromatic ring is pyridine it is optionally in the form of the N-oxide;

Y is optionally branched C$_{1-4}$alkylidene optionally substituted by an oxo group;

Z is pyrazine, pyrimidine or a 5-membered heteroaromatic ring containing at least one nitrogen or an oxygen and optionally 1, 2 or 3 other heteroatoms independently selected from oxygen, nitrogen and sulphur, at most one of the other heteroatoms being oxygen or sulphur, the ring being optionally substituted by a group $R^1$, $NR^2R^3$, $NR^2COR^3$, CN, $CF_3$, phenyl, benzyl or pyridyl or a 5-membered heteroaromatic ring containing at least one nitrogen or an oxygen and optionally 1, 2 or 3 other heteroatoms independently selected from oxygen, nitrogen and sulphur, at most one of the other heteroatoms being oxygen or sulphur:

$R^1$ is $C_{1-6}$alkyl, $C_{2-6}$alkenyl, $C_{2-6}$alkynyl or $CF_3$;

$R^2$ and $R^3$ are each independently hydrogen, $C_{1-6}$alkyl, $C_{2-6}$alkenyl, $C_{2-6}$alkynyl or $CF_3$ or $R^2$ and $R^3$, together with the nitrogen atom to which they are attached, form a 4–7 membered ring; and n is 1 or 2;

or a pharmaceutically acceptable salt thereof or a prodrug thereof.

In one embodiment there is provided a compound of formula I':

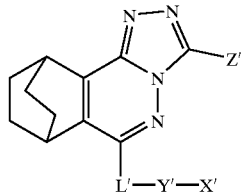

(I')

wherein L', X', Y' and Z' are as defined for L, X, Y and Z, or a pharmaceutically acceptable salt thereof or a prodrug thereof.

As used herein, the expression "$C_{1-6}$alkyl" includes methyl and ethyl groups, and straight-chained, branched or cyclic propyl, butyl, pentyl and hexyl groups. Particular alkyl groups are methyl, ethyl, n-propyl, isopropyl and t-butyl and cyclohexyl. Derived expressions such as "$C_{2-6}$alkenyl" and "$C_{2-6}$alkynyl" are to be construed in an analogous manner.

Suitable 5- and 6-membered heteroaromatic rings include pyridinyl, pyridazinyl, pyrimidinyl, pyrazinyl, furyl, thienyl, pyrrolyl, pyrazolyl, oxazolyl, isoxazolyl, thiazolyl, isothiazolyl, imidazolyl, oxadiazolyl and thiadiazolyl groups.

The term "halogen" as used herein includes fluorine, chlorine, bromine and iodine, especially fluorine, chlorine and bromine.

It will be understood that the fused ring containing the $(CH_2)n$ moiety is, when n=2 a [2.2.2]bicyclo-octenyl ring and when n=1 a [2.2.1]bicycloheptenyl ring.

Preferably L is an oxygen atom.

Preferably X is pyridinyl optionally fused to a benzene ring and optionally in the form of the N-oxide, or X is phenyl, imidazolyl or thiazolyl and X is optionally substituted by one or two groups chosen from $C_{1-6}$alkyl, cyano and halogen, preferably chosen from methyl, cyano and bromine, or X is a group $NR^2R^3$ in which $R^2$ and $R^3$ independently, represent $C_{1-6}$alkyl or form a 4–7 membered ring, preferably a five membered ring, together with the nitrogen atom to which they are attached.

Apt values for Y include $CH_2$, $CH(CH_3)$, $CH_2CH_2$ and $CH_2CH_2CH_2$ optionally substituted by an oxo group. Preferably Y is $CH_2$ or $CH_2CO$ and most preferably $CH_2$.

Suitable groups Z include pyrimidinyl, pyrazinyl, pyrrolyl, oxazolyl, isoxazolyl, thiazolyl, isothiazolyl, oxadiazolyl and thiadiazolyl which groups are optionally substituted by $C_{1-6}$alkyl, pyridyl or amino.

Favoured values for Z include furans, pyrimidines, pyrazines, isoxazoles, oxazoles, thiazoles, oxadiazoles and thiadiazoles each of which is optionally substituted by $C_{1-6}$alkyl, pyridyl or amino. More preferably Z is an oxadiazole, furan, pyrimidine, pyrazine, oxazole or isoxazole optionally substituted by $C_{1-6}$alkyl or pyridyl. More preferably still Z is optionally substituted by methyl, ethyl, isopropyl or pyridyl.

In one embodiment, as mentioned above, the present invention provides compounds of formula $I^1$ which are preferably substituted as indicated above.

In a further embodiment there is provided a compound of formula I":

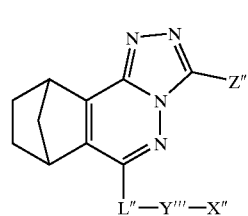

(I")

wherein L", X''', Y''' and Z" are as defined for L, X, Y and Z above.

In a particularly preferably embodiment of the compound of formula I", L" is O, Y" is $CH_2$, X''' is pyridyl which is unsubstituted or substituted by $C_{1-6}$alkyl and Z" is a furan, isoxazole or pyrazine which is unsubstituted or substituted by $C_{1-6}$alkyl.

Preferably X" is isoxazolyl, furyl or pyrazinyl which is unsubstituted or substituted by methyl, more particularly X" is methylisoxazolyl, furyl or pyrazinyl.

Preferably Z" is isoxazolyl or furyl which is unsubstituted or substituted by methyl, more particularly Z" is methylisoxazolyl or furyl.

In one embodiment of the invention Z is not furyl.

For use in medicine, the salts of the compounds of formula I will be pharmaceutically acceptable salts. Hence in a favoured aspect this invention provides the compounds of the formula I and pharmaceutically acceptable salts thereof. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Designs of Prodrugs,* ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

One apt group of compounds of this invention are of the formula (II):

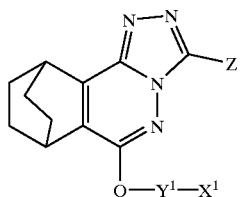

(II)

and pharmaceutically acceptable salts thereof wherein Z is as defined in relation to formula (I); X¹ is: a 6-membered heteroaromatic ring containing one or two nitrogen atoms optionally substituted by one or two $C_{1-6}$ alkyl groups which ring is optionally fused to a benzene ring and when the 6-membered heterocycle is pyridine it is optionally in the form of the N-oxide: a 5-membered heteroaromatic ring containing one or two nitrogen atoms and optionally one additional heteroatom selected from nitrogen, oxygen or sulphur and optionally substituted by $C_{1-6}$alkyl; an amine of the formula $NR^{10}R^{11}$ where $R^{10}$ and $R^{11}$ are independently hydrogen or $C_{1-6}$alkyl or are joined to form together with the nitrogen atom to which they are attached to form a 4–7 membered ring; or a phenyl ring optionally substituted by Br or CN: and Y¹ is $CH_2$ or CHCO.

Particular values of X¹ include cyanophenyl, bromophenyl, thiazolyl, pyridinyl, methylpyridinyl, dimethylpyridinyl, N-oxopyridinyl fused benzene pyridinyl, imidazolyl and N-methylimidazolyl.

Specific compounds within the scope of the present invention include:

3-(5-methylisoxazol-3-yl)-6-(6-methylpyridin-2-yl)methyloxy-7,8,9,10-tetrahydro-(7,10-ethano)-1,2,4-triazolo[3,4-a]phthalazine;

3-(3-furyl)-6-(6-methylpyridin-2-yl)methyloxy-7,8,9,10-tetrahydro-(7,10-ethano)-1,2,4-triazolo[3,4-a]phthalazine;

3-(2-furyl)-6-(2-pyridyl)methyloxy-7,8,9,10-tetrahydro-(7,10-ethano)-1,2,4-triazolo [3,4-a]phthalazine;

6-(6-methylpyridin-2-yl)methyloxy-3-(2-pyrazinyl)-7,8,9,10-tetrahydro-(7,10-ethano)-1,2,4-triazolo[3,4-a]phthalazine;

3-(3-methyl-1,2,4-oxadiazol-5-yl)-6-(6-methylpyridin-2-yl)methyloxy-7,8,9,10-tetrahydro-(7,10-ethano)-1,2,4-triazolo[3,4-a]phthalazine;

3-(3-methyl-1,2,4-oxadiazol-5-yl)-6-(2-pyridyl)methyloxy-7,8,9,10-tetrahydro-(7,10-ethano)-1,2,4-triazolo[3,4-a]phthalazine;

3-(3-methyl-1,2,4-oxadiazol-5-yl)-6-(3-pyridyl)methyloxy-7,8,9,10-tetrahydro-(7,10-ethano)-1,2,4-triazolo[3,4-a]phthalazine;

6-(5,6-dimethylpyridin-2-yl)methyloxy-3-(3-methyl-1,2,4-oxadiazol-5-yl)-7,8,9,10-tetrahydro-(7,10-ethano)-1,2,4-triazolo[3,4-a]phthalazine:

6-(4,6-dimethylpyridin-2-yl)methyloxy-3-(3-methyl-1,2,4-oxadiazol-5-yl)-7,8,9,10-tetrahydro-(7,10-ethano)-1,2,4-triazolo[3,4-a]phthalazine;

3-(3-methyl-1,2,4-oxadiazol-5-yl)-6-(2-quinolino)methyloxy-7 8,9,10-tetrahydro-(7,10-ethano)-1,2,4-triazolo [3,4-a]phthalazine;

3-(3-methyl-1,2,4-oxadiazol-5-yl)-6-(2-pyridyl-N-oxide)methyloxy-7,8,9,10-tetrahydro-(7,10-ethano)-1,2,4-triazolo[3,4-a]phthalazine;

6-(2-imidazolyl)methyloxy-3-(3-methyl-1,2,4-oxadiazol-5-yl)-7,8,9,10-tetrahydro-(7,10-ethano)-1,2,4-triazolo[3,4-a]phthalazine;

6-[2-(1-methyl)imidazolyl]methyloxy-3-(3-methyl-1,2,4-oxadiazol-5-yl)-7,8,9,10-tetrahydro-(7,10-ethano)-1,2,4-triazolo[3,4-a]phthalazine:

6-[2-(cyano)phenyl]methyloxy-3-(3-methyl-1,2,4-oxadiazol-5-yl)-7,8,9,10-tetrahydro-(7,10-ethano)-1,2,4-triazolo[3,4-a]phthalazine;

6-(2-bromophenyl)methyloxy-3-(3-methyl-1,2,4-oxadiazol-5-yl)-7,8,9,10-tetrahydro-(7,10-ethano)-1,2,4-triazolo[3,4-a]phthalazine;

3-(3-methyl-1,2,4-oxadiazol-5-yl)-6-(4-thiazolo)methyloxy-7,8,9,10-tetrahydro-(7,10-ethano)-1,2,4-triazolo[3,4-a]phthalazine;

3-(3-methyl-1,2,4-oxadiazol-5-yl)-6-(N-pyrrolidinylcarbonyl)methyloxy-7,8,9,10-tetrahydro-(7,10-ethano)-1,2,4-triazolo[3,4-a]phthalazine;

3-(3-ethyl-1,2,4-oxadiazol-5-yl)-6-(6-methylpyridin-2-yl)methyloxy-7,8,9,10-tetrahydro-(7,10-ethano)-1,2,4-triazolo[3,4-a]phthalazine;

3-(3-isopropyl-1,2,4-oxadiazol-5-yl)-6-(6-methylpyridin-2-yl)methyloxy-7,8,9,10-tetrahydro-(7,10-ethano)-1,2,4-triazolo[3,4-a]phthalazine;

6-(6-methylpyridin-2-yl)methyloxy-3-[3-(pyridin-3-yl)-1,2,4-oxadiazol-5-yl]-7,8,9,10-tetrahydro-(7,10-ethano)-1,2,4-triazolo[3,4-a]phthalazine;

6-(6-methylpyridin-2-yl)methyloxy-3-[3-(pyridin-4-yl)-1,2,4-oxadiazol-5-yl]-7,8,9,10-tetrahydro-(7,10-ethano)-1,2,4-triazolo[3,4-a]phthalazine;

6-(5,6-dimethylpyridin-2-yl)methyloxy-3-[3-(pyridin-3-yl)-1,2,4-oxadiazol-5-yl]-7,8,9,10-tetrahydro-(7,10-ethano)-1,2,4-triazolo[3,4-a]phthalazine;

3-(2-methyloxazol-4-yl)-6-(2-pyridyl)methyloxy-7,8,9,10-tetrahydro-(7,10-ethano)-1,2,4-triazolo[3,4-a]phthalazine;

3-(2-methyloxazol-4-yl)-6-(6-methylpyridin-2-yl)methyloxy-7,8,9,10-tetrahydro-(7,10-ethano)-1,2,4-triazolo[3,4-a]phthalazine;

and pharmaceutically acceptable salts and prodrugs thereof.
Further specific compounds are:

3-(5-methylisoxazol-3-yl)-6-(2-pyridyl)methyloxy-7,8,9,10-tetrahydro-(7,10-ethano)-1,2,4-triazolo[3,4-a]phthalazine;

3-(5-methylisoxazol-3-yl)-6-(2-cyanophenyl)methyloxy-7,8,9,10-tetrahydro-(7,10-ethano)-1,2,4-triazolo[3,4-a]phthalazine:

6-(3-methylpyridin-2-yl)methyloxy-3-(2-pyrazinl)-7,8,9,10-tetrahydro-(7,10-ethano)-1,2,4-triazolo[3,4-a]phthalazine:

3-(2-pyrazinyl)-6-(2-pyridyl)methyloxy-7,8,9,10-tetrahydro-(7,10-ethano)-1,2,4-triazolo[3,4-a]phthalazine;

3-(5-methylisoxazol-3-yl)-6-(2-pyridyl)methyloxy-7,8,9,10-tetrahydro-(7,10-methano)-1,2,4-triazolo[3,4-a]phthalazine;

3-(5-methylisoxazol-3-yl)-6-(6-methylpyridin-2-yl)methyloxy-7,8,9,10-tetrahydro-(7,10-methano)-1,2,4-triazolo[3,4-a]phthalazine;

3-(3-furyl)-6-(2-pyridyl)methyloxy-7,8,9,10-tetrahydro-(7,10-ethano)-1,2,4-triazolo[3,4-a]phthalazine;

and pharmaceutically acceptable salts and prodrugs thereof.

The compounds of the present invention have a binding affinity ($K_i$) for the $\alpha_5$ subunit of 100 nM or less, typically 50 nM or less and preferably of 10 nM or less. In a preferred embodiment the compounds of the invention possess at least a 2-fold, suitably at least a 5-fold and advantageously at least a 10-fold, most preferably at least a 50-fold binding selectivity for the $\alpha_5$ subunit relative to the $\alpha_1$, $\alpha_2$ and $\alpha_3$ subunits.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human or animal body. Preferably the treatment is for a condition associated with $GABA_A$ receptors comprising the $\alpha_5$ subunit and/or for the enhancement of cognition.

The present invention further provides the use of a compound of the present invention in the manufacture of a medicament for the enhancement of cognition.

Also disclosed is a method of treatment of a subject suffering from a cognition deficit which comprises administering to that subject an effective amount of a compound according to the present invention.

The liquid forms in which the novel compositions of the present invention may be incorporated for administration orally or by injection include aqueous solutions, suitably flavoured syrups. aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

For the enhancement of cognition, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

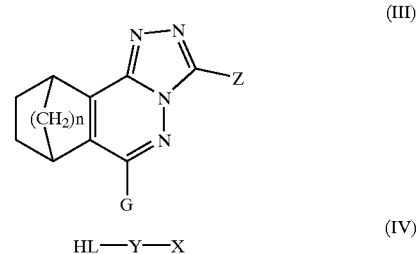

wherein n, L, X, Y and Z are as defined above and G is a leaving group such as chlorine.

Compounds of formula III represent a further feature of the present invention. The groups Z which are preferred for compounds of formula I are preferred for these compounds likewise.

The reaction between compounds III and IV is conveniently effected by stirring the reactants in a suitable solvent, typically N,N-dimethyl-formamide, in the presence of a strong base such as sodium hydride or lithium hexamethyldisilylazide, typically without heating.

The intermediates of formula III above may be prepared by reacting a compound of formula V, which constitutes a further feature of the present invention, with a compound of formula VI:

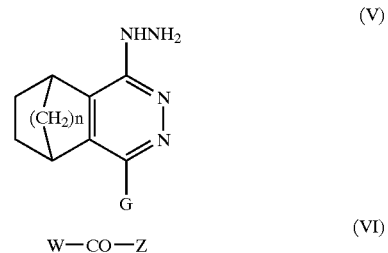

wherein G, n and Z are as defined above, and W represents a suitable leaving group such as a carboxylic acid ester, chlorine or hydroxy.

The reaction is advantageously conducted in an inert organic solvent and generally in the presence of an organic nitrogen base. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from room temperature to the reflux temperature of the reaction mixture, for a period of time that depends on the reactants employed and the temperature at which the reaction is carried out. The compound of formula VI may be activated before reaction by reacting with a compound such as 1,1'-dicarbonyldiimide to form the ketohydrazine.

The compound of formula (V) is prepared by reaction of a compound of formula (VII):

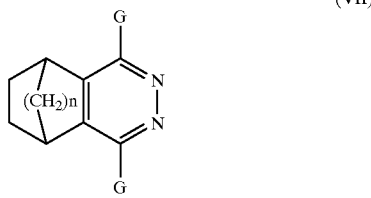

(VII)

where G and n are as defined above, with hydrazine, usually in the form of its monohydrate, generally in a solvent such as ethanol and generally by refluxing for a suitable period such as 14–24 hours.

Where they are not commercially available, the starting materials of formula IV, VI and VII may be prepared by methods analogous to those described in the accompanying Examples, or by standard methods known from the art.

It will be understood that any compound of formula I initially obtained from the above process may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α5 subunit stably expressed in Ltk⁻cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells: 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]Ro 15-1788 from the α5 subunit of the human $GABA_A$ receptor of 25 nM or less.

REFERENCE EXAMPLE 1

3-Chloro-6-hydrazino-4,5-diazatricyclo[6,2,2,7]dodeca-2(7),3,5-triene a) 4,5-Diazatricyclo[6.2.2.2,7]dodec-2(7)-ene-3,6-dione Bicyclo[2.2.2]oct-2-ene-2,3-dicarboxylic acid anhydride (prepared as described in *J. Org. Chem.*, 1993, 6740–6744) (60.8 g, 0.342 mol) was dissolved in 50% aqueous acetic acid (1600 ml) with sodium acetate trihydrate (55.5 g, 1.2 mol eq) and hydrazine hydrate (19.82 ml, 1.2 mol eq). The reaction mixture was heated under reflux for 16 h then allowed to cool. The solid produced was collected by filtration and washed with water and diethyl ether before drying in a vacuum oven at 80° C. to give the required product (59.3 g, m.p.=214° C.). $^1$H NMR (250 MHz, DMSO) δ1.16 (4H, d, J=7.1 Hz), 1.69 (4H, d, J=7.1 Hz), 3.18 (2H, s), 11.31 (2H, br, s, NH); MS (ES⁺) m/e 193 [MH]⁺.

b) 3,6-Dichloro-4,5-diazatricyclo[6.2.2.2,7]dodeca-2(7),3,5-triene

The product from Example 1 Step a) (59.2 g) was dissolved in phosphorus oxychloride (300 ml) and heated under reflux for 14 h. The solvent was removed under vacuum and azeotroped 2× toluene. The residue was dissolved in dichloromethane (200 ml) and stirred rapidly and the solution was neutralised by the addition of solid and aqueous sodium hydrogen carbonate (cautiously). When effervescence had ceased, the organic layer was separated and the aqueous layer was extracted with dichloromethane (2×200 ml). The combined organic layers were dried (MgSO$_4$), filtered and evaporated to give the required product (59.5 g, m.p. >370° C.). $^1$H NMR (250 MHz. CDCl$_3$) δ1.39 (4 H, d, J=8.1 Hz), 1.92 (4 H, d, J=8.1 Hz), 3.47 (2 H, s); MS (ES$^+$) m/e 299 [MH]$^+$.

c) 3-Chloro-6-hydrazino-4,5-diazatricyclo[6.2.2,7] dodeca-2(7),3,5-triene

The preceding product (40.0 g, 0.175 mol) was added to a stirred solution of hydrazine monohydrate (56.8 g, 1.13 mol) in ethanol (600 ml) and the solution refluxed for 18 h. The mixture was cooled to room temperature and the solvent removed in vacuo. Water (150 ml) was added to the residue and the mixture acidified to pH 1–2 with 5N hydrochloric acid. The aqueous was extracted with dichloromethane (×3) and then basified with powdered K$_2$CO$_3$ and extracted with dichloromethane (×3). The combined dichloromethane was dried (MgSO$_4$) and evaporated to give a pale yellow solid (29.0 g, 78%), mp 136–140° C., $^1$H NMR (250 MHz, CDCl$_3$) δ1.27–1.45 (4H, m, 2, of CH$_2$), 1.79–1.91 (4H, m, 2, of CH$_2$), 3.05 (1H, s, CH), 3.40 (1H, s, CH), 3.94 (2H, br s, NH$_2$NH), 6.18 (1H, br s, NHNH$_2$); MS (ES$^+$) m/e 225 [MH]$^+$.

Example 1

3-(5-Methylisoxazol-3-yl)-6-(6-methylpyridin-2-yl) methyloxy-7,8,9,10-tetrahydro-(7,10-ethano)-1,2,4-triazolo[3,4-a]phthalazine a) 6-Chloro-3-(5-methylisoxazol-3-yl)-7,8,9,10-tetrahydro-(7,10-ethano)-1,2,4-triazolo[3,4-a] phthalazine 1,1'-Carbonyldiimidazole (2.0 g, 12.6 mmol) was added to a stirred solution of 5-methylisoxazole-3-carboxylic acid in DMF (50 ml). The solution was stirred for 0.5 h before adding the preceding hydrazine (2.63 g, 11.7 mmol). After 1 h at room temperature, the solution was poured into water and the resultant precipitate was filtered, washed with water (30 ml) and hexane (100 ml), and dried in vacuo to give the ketohydrazine (3.1 g, 79%); MS (ES$^+$) m/e 334 [MH]$^+$. A solution of the ketohydrazine (1.0 g, 3.0 mmol) and triethylamine hydrochloride (0.2 g, 1.45 mmol), in xylene (30 ml), was heated at reflux for 4 h. The solution was cooled to room temperature and the solvent removed in vacuo. The residue was chromatographed through silica gel, eluting with ethyl acetate, to give the title-phthalazine (0.60 g, 63%), mp 186–188° C.; $^1$H NMR (250 MHz, CDCl$_3$) δ1.22–1.54 (4H, m, 2 of CH$_2$), 1.94–2.06 (4H, m, 2 of CH$_2$), 2.58 (3H, s, Me), 3.60 (1H, s, CH), 4.08 (1H, s, CH), 6.90 (1H, s, Ar—H); MS (ES$^+$) m/e 316 [MH]$^+$.

b) 3-(5-Methylisoxazol-3-yl)-6-(6-methylpyridin-2-yl)methyloxy-7,8,9,10-tetrahydro-(7,10-ethano)-1,2,4-triazolo[3,4-a]phthalazine To a solution of 6-methyl-2-pyridylcarbinol (0.47 g, 3.8 mmol), in DMF (50 ml), was added sodium hydride (0.15 g of a 60% dispersion in oil, 3.8 mmol) and the mixture was stirred at room temperature for 0.25 h. After this time, the preceding product (1.0 g, 3.2 mmol) was added and the reaction mixture stirred at 55° C. for 16 h. The solvent was removed under vacuum and the residue partitioned between ethyl acetate and water. The aqueous was separated and extracted further with ethylacetate (×3). The combined extracts were dried (Na$_2$SO$_4$/MgSO$_4$) and evaporated, and the residue chromatographed on silica gel eluting with ethyl acetate to give the required product (0.35 g, 28%), mp 223–225° C.; $^1$H NMR (250 MHz CDCl$_3$) δ1.38–1.54 (4H, m, 2 of CH$_2$), 1.84–1.98 (4H, m, 2 of CH$_2$), 2.58 (3H, s, Me), 2.60 (3H, s, Me), 3.58 (1H, s CH), 3.98 (1H, s, CH), 5.59 (2H, s, CH$_2$), 6.85 (1H, s, Ar—H), 7.14 (1H, d, J=7.7 Hz), 7.44 (1H, d, J=7.6 Hz, Ar—H), 7.64 (1H, dd, J=7.7 and 7.6 Hz, Ar—H); MS (ES$^+$) m/e 403 [MH]$^+$. Anal. Found C, 64.91; H, 5.38; N, 20.28. C$_{22}$H$_{22}$N$_6$O$_2$.0.3H$_2$O requires C, 64.79: H, 5.58; N, 20.60 %.

Example 2

3-(3-Furyl)-6-(6-methylpyridin-2-yl)methyloxy-7,8,9,10-tetrahydro-(7,10-ethano)-1,2,4-triazolo[3,4-a]phthalazine.

a) 6-Chloro-3-(3-furyl)-7,8,9,10-tetrahydro-(7,10-ethano)-1,2,4-triazolo[3,4-a]phthalazine To a solution of 3-chloro-6-hydrazino-4,5-diazatricyclo [6.2.2,7]dodeca-2(7),3,5-triene (1.0 g, 4.45 mmol), in xylene (20 ml), was added triethylamine (0.67 g, 6.7 mmol) and 3-furoyl chloride (0.58 g, 4.4 mmol). The mixture was stirred at room temperature for 1 h and then heated at reflux for 16 h. The solution was cooled to room temperature, the solvent evaporated under reduced pressure, and the residue partitioned between dichloromethane (150 ml) and water (30 ml). The aqueous was separated and extracted further with dichloromethane (×2). The combined extracts were dried (Na$_2$SO$_4$), evaporated, and the residue chromatographed on silica gel eluting with ethyl acetate to afford the title-product (0.75 g, 56%); $^1$H NMR (250 MHz, CDCl$_3$) δ1.41–1.55 (4H, m, 2 of CH$_2$), 1.90–2.05 (4H, m, 2 of CH$_2$), 3.57 (1H, s, CH), 4.04 (1H, s, CH), 7.30–7.31 (1H, m, Ar—H), 7.59–7.60 (1H, m, Ar—H), 8.61 (1H, s, Ar—H); MS (ES$^+$) m/e 301 [MH]$^+$.

b) 3-(3-Furyl)-6-(6-methylpyridin-2-yl)methyloxy-7,8,9,10-tetrahydro-(7,10-ethano)-1,2,4-triazolo[3,4-a] phthalazine The title-compound was prepared from the preceding product and 6-methyl-2-pyridylcarbinol using the procedure given for Example 1 part b, mp 205–206 ° C.; $^1$H NMR (250 MHz, CDCl$_3$) δ1.38–1.56 (4H, m, 2 of CH$_2$), 1.84–2.02 (4H, m, 2 of CH$_2$), 2.63 (3H, s, Me), 3.58 (1H, s, CH), 3.96 (1H, s, CH), 5.58 (2H, s, CH$_2$), 7.14 (1H, d, J=7.6 Hz, Ar—H), 7.26 (1H, s, Ar—H), 7.31 (1H, d, J=7.7 Hz, Ar—H), 7.55–7.56 (1H, m, Ar—H), 7.64 (1H, dd, J=7.7 and 7.6 Hz, Ar—H), 8.50 (1H, s, Ar—H); MS (ES$^+$) m/e 388 [MH]$^+$; Anal. Found C, 67,23; H, 5.41; N, 17.51. C$_{22}$H$_{21}$N$_5$O$_2$.0.25 H$_2$O requires C. 67.41; H, 5.53; N, 17.87%).

Example 3

3-(2-Furyl)-6-(2-pyridyl)methyloxy-7,8,9,10-tetrahydro-(7,10-ethano)-1,2,4-triazolo[3.4-a] phthalazine The title-compound was prepared from 3-chloro-6-hydrazino-4,5-diazatricyclo[6.2.2.2,7]dodeca-2(7),3,5-triene and 2-furoyl chloride using the procedure described for Example 2 part a. The resultant triazolopyridazine was reacted with 2-pyridylcarbinol using the procedure described for Example 1 part b to afford the desired product, mp 245° C.; $^1$H NMR (360 MHz, CDCl$_3$) δ1.40–1.56 (4H, m, 2 of CH$_2$), 1.86–1.98 (4H, m, 2 of CH$_2$), 3.58 (1H, s, CH), 3.99 (1H, s, CH), 5.65 (2H, s, CH$_2$), 6.61–6.62 (1H, m, Ar—H), 7.28–7.31 (1H, m, Ar—H), 7.39 (1H, d, J=3.5 Hz, Ar—H), 7.54 (1H, d, J=7.7 Hz, Ar—H), 7.65 (1H, s, Ar—H), 7.75–7.79 (1H, m, Ar—H), 8.64–8.66 (1H, m, Ar—H); MS (ES$^+$) m/e 374 [MH]$^+$; Anal. Found C, 67,37; H, 5.03; N, 18.80. C$_{21}$H$_{19}$N$_5$O$_2$ requires C, 67.55; H, 5.13; N, 18.76%.

Example 4

6-(6-Methylpyridin-2-yl)methyloxy-3-(2-pyrazinyl)-7,8,9,10-tetrahydro-(7,10-ethano)-1.2.4-triazolo[3,4-a]phthalazine a) 6-Chloro-3-(2-Pyrazinyl)-7,8,9,10-tetrahydro-(7,10-ethano)-1,2,4-triazolo[3,4-a]phthalazine The title-compound was prepared from 3-chloro-6-hydrazino-4,5-diazatricyclo[6.2.2.2,7]dodeca-2(7), 3,5-triene and pyrazine-2-carboxylic acid using the procedure described for Example 1 part a; $^1$H NMR (250 MHz, CDCl$_3$) 1.40–1.56 (4H, m, 2 of CH$_2$), 1.90–2.08 (4H, m, 2 of CH$_2$), 3.61 (1H, s, CH), 4.12 (1H, s, CH), 8.74 (1H, d, J=1.5 Hz, Ar—H), 8.86 (1H, dd, J=1.3 and 1.5 Hz, Ar—H), 9.72 (1H, d, J=1.3 Hz, Ar—H), MS (ES$^+$) m/e 313 [MH]$^+$.

b) 6-(6-Methylpyridin-2-yl)methyloxy-3-(2-pyrazinyl)-7,8,9,10-tetrahydro-(7,10-ethano)-1,2,4-triazolo[3,4-a]phthalazine To a solution of 6-methyl-2-pyridylcarbinol hydrochloride (0.275 g, 1.72 mmol), in DMF (10 ml), was added NaH (0.138 g of 60% dispersion in oil, 3.45 mmol) and the mixture was stirred at room temperature for 0.25 h. The product from Example 4 step a (0.225 g, 0.72 mmol) was added and the mixture stirred at room temperature for 2 h and then at 60° C. for 15 h. The solvent was removed under vacuum and the residue partitioned between water (20 ml) and ethyl acetate (100 ml). The aqueous was extracted further with ethyl acetate (×2) and the combined organic was dried (MgSO$_4$) and evaporated. The residue was triturated with ethyl acetate to give the title-compound (0.16 g, 56%), mp 204–206 ° C.; $^1$H NMR (360 MHz, CDCl$_3$) δ1.40–1.56 (4H, m, 2 of CH$_2$), 1.87–2.02 (4H, m, 2 of CH$_2$), 2.61 (3H, s, Me), 3.60 (1H, s, CH), 4.03 (1H, s, CH), 5.57 (2H, s, CH$_2$), 7.14 (1H, d, J=7.7 Hz, Ar—H), 7.35 (1H, d, J=7.7 Hz, Ar—H), 7.64 (1H, dd, J=7.7 and 7.7 Hz, Ar—H), 8.68 (1H, d, J=1.5 Hz, Ar—H), 8.82 (1H, dd, J=1.3 and 1.5 Hz, Ar—H), 9.65 (1H, d, J=1.3 Hz, Ar—H); MS (ES$^+$) m/e 400 [MH]$^+$.

Example 5

3-(3-Methyl-1,2,4-oxadiazol-5-yl)-6-(6-methylpyridin-2-yl)methyloxy-7,8,9,10-tetrahydro-(7,10-ethano)-1,2,4-triazolo[3,4-a]phthalazine Intermediate 1

6-Chloro-3-(3-methyl-1,2,4-oxadiazol-5-yl)-7.8.9,10-tetrahydro-(7,10-ethano)-1,2,4-triazole[3,4-a]phthalazine a) Ethyl-[3-(methyl)-1,2,4-oxadiazol-5-yl)]carboxylate Pyridine (32.7 ml, 0.404 mol) was added dropwise to a stirred suspension of acetamide oxime (10.0 g, 0.135 mol), in 1.2-dichloroethane, at room temperature, under nitrogen. The mixture was cooled to 0° C., and ethyl oxalyl chloride (22.6 ml, 0.202 mol) was added dropwise over 0.2 h. After stirring at 0° C. for 0.1 h the mixture was warmed to room temperature for 0.3 h and then to 80° C. and stirred for 2.1 h. The mixture was diluted with CH$_2$Cl$_2$ (200 ml) and washed with 2N HCl (100 ml), H$_2$O (2×100 ml) and brine (100 ml). The solution was dried (MgSO$_4$) and evaporated in vacuo to give the title oxadiazole (20.05 g, 95%); $^1$H NMR (250 MHz, CDCl$_3$) δ1.46 (3H, t, J=7.2 Hz, Me), 2.52 (3H, s, Me), 4.55 (2H, q, J=7.2 Hz, CH$_2$).

b) 6-Chloro-3-(3-methyl-1,2,4-oxadiazol-5-yl)-7,8,9.10-tetrahydro-(7,10-ethano)-1,2,4-triazolo[3.4-a]phthalazine Ethyl-[3-(methyl)-1,2,4-oxadiazol-5-yl]carboxylate (0.987 g, 6.32 mmol) was added to a solution of 3-chloro-6-hydrazino-4,5-diazatricyclo[6.2.2.2,7]dodeca-2(7),3,5-triene (1.18 g, 5.3 mmol) in anhydrous dioxane (28 ml) and the reaction mixture stirred at reflux for 3 days. The solvent was removed under vacuum and the residue was partitioned between dichloromethane (120 ml) and water (30 ml). The dichloromethane was separated, dried (MgSO$_4$) and evaporated in vacuo and the residue chromatographed on silica gel eluting with 15% ethyl acetate/dichloromethane to give the title-product (0.32 g, 19%); 1H NMR (360 MHz, CDCl$_3$) δ1.42–1.57 (4H, m, 2 of CH$_2$), 1.95–2.08 (4H, m, 2 of CH$_2$), 2.62 (3H, s, Me), 3.64 (1H, s, CH), 4.13 (1H, s, CH); MS (ES$^+$) m/e 317 [MH]$^+$.

3-(3-Methyl-1,2,4-oxadiazol-5-yl)-6-(6-methylpyridin-2-yl)methyloxy -7,8,9,10-tetrahydro-(7,10-ethano)-1,2,4-triazolo[3.4-a]phthalazine The title-compound was prepared from the preceding product and 6-methyl-2-pyridinylcarbinol hydrochloride using the procedure given for Example 4 part b, mp 191–193° C.: $^1$H NMR (360 MHz, CDCl$_3$) δ1.38–1.56 (4H, m, 2 of CH$_2$), 1.86–2.03 (4H, m, of CH$_2$), 2.60 (3H, s, Me), 2.60 (3H, s, Me), 3.62 (1H, s, CH), 4.02 (1H, s, CH), 5.62 (2H, s, CH), 7.14 (1H, d, J=7.7 Hz, Ar—H), 7.49 (1H, d, J=7.7 Hz, Ar—H), 7.65 (1H, dd, J=7.7 and 7.7 Hz, Ar—H); MS (ES$^+$) m/e 404 [MH]$^+$; Anal. Found C, 61.90; H, 5.10; N, 23.50. C$_{21}$H$_{21}$N$_7$O$_2$. 0.1(ethyl acetate). 0.2H$_2$O requires C, 61.81; H, 5.38; N, 23.58%.

Example 6

3-(3-Methyl-1,2,4-oxadiazol-5-yl)-6-(2-pyridyl)methyloxy-7,8,9,10-tetrahydro-(7,10-ethano)-1,2,4-triazolo[3,4-a]phthalazine The title-compound was prepared from Intermediate 1 and 2-pyridylcarbinol using the procedure given for Example 4 part b, mp 182° C.; $^1$H NMR (360 MHz, CDC$_3$) δ1.40–1.53 (4H, m, 2 of CH$_2$), 1.89–2.00 (4H, m, 2 of CH$_2$), 2.60 (3H, s, Me), 3.61 (1H, s, CH), 4.02 (1H, s, CH), 5.66 (2H, s, CH$_2$), 7.29 (1H, m, Ar—H), 7.72 (1H, t, J=7.8 Hz, Ar—H), 7.77 (1H, dd, J=7.6 and 6.1 Hz, Ar—H), 8.64 (1H, m, Ar—H); MS (ES$^+$) m/e 390 [MH]$^+$; Anal. Found C, 61.56; H, 4.96; N, 24.72. C$_{20}$H$_{19}$N$_7$O$_2$. 0.1H$_2$O requires C, 61.40; H, 4.95; N, 25.06%.

Example 7

3-(3-Methyl-1,2,4-oxadiazol-5-yl)-6-(3-pyridyl)methyloxy-7,8,9,10-tetrahydro-(7,10-ethano)-1,2,4-triazolo[3,4-a]phthalazine Sodium hydride(63 mg of a 60% dispersion in oil, 1.6 mmol) was added to a stirred solution of 3-pyridylcarbinol (112 mg, 1.03 mmol) in DMF (8 ml) at room temperature under nitrogen and the mixture stirred for 0.8 h. After this time, Intermediate 1 (250 mg, 0.789 mmol) was added and the reaction mixture stirred for 22 h. Water (34 ml) was added and the resulting precipitate stirred for 1.25 h before being collected by filtration. Flash chromatography on silica gel eluting with ethyl acetate followed by recrystallisation (ethyl acetate/diethyl ether) gave the title-product (132 mg, 43%), mp 167.5–168° C.; $^1$H NMR (360 MHz, CDCl$_3$) δ1.36–1.52 (4H, m, 2 of CH$_2$), 1.89–2.00 (4H, m, 2 of CH$_2$), 2.63 (3H, s, Me), 3.53 (1H, br s, CH), 4.01 (1H, br s, CH), 5.59 (2H, s, CH$_2$), 7.37 (1H, dd, J=7.6 and 5.0 Hz, Ar—H), 8.02 (1H, br d, J=7.9 Hz, Ar—H), 8.62 (1H, d, J=5.0 Hz, Ar—H), 8.90 (1H, s, Ar—H); MS (ES$^+$) m/e 390 [MH]$^+$; Anal. Found C, 61.44; H, 4.94; N, 24.89. C$_{20}$H$_{19}$N$_7$O requires C, 61.69; H, 4.92; N, 25.18%.

Example 8

6-(5,6-Dimethylpyridin-2-yl)methyloxy-3-(3-methyl-1,2,4-oxadiazol-5-yl)-7,8,9,10-tetrahydro-(7,10-ethano)-1,2,4-triazolo[3,4-a]phthalazine The title-compound was prepared from Intermediate 1 and 2-hydroxymethyl-5,6-dimethylpyridine (prepared as described in patent WO 93/21158) using lithium hexamethyldisilylazide as base, following the procedure given for Example 7, mp 139–141° C.; $^1$H NMR (250 MHz, CDCl$_3$) δ1.38–1.60 (4H, m, 2 of CH$_2$), 1.86–2.00 (4H, m, 2 of CH$_2$), 2.31 (3H, 2.55 (3H, s, Me), 2.61 (3H, s, Me), 3.60 (1H, br s, CH), 4.01 (1H, br s, CH), 5.61 (2H, s, CH$_2$), 7.48 (2H, s, Ar—H); MS (ES$^+$) m/e 418 [MH]$^+$.

Example 9

6-(4,6-Dimethylpyridin-2-yl)methyloxy-3-(3-methyl-1,2,4-oxadiazol-5-yl)-7,8,9,10-tetrahydro-(7,10-ethano)-1,2,4-triazolo[3,4-a]phthalazine The title-compound was prepared from Intermediate 1 and 2-hydroxymethyl-4,6-dimethylpyridine (prepared in an analogous manner to that described in *J. Am. Chem. Soc.*, 1954, 76, 1286) using the procedure given for Example 8, mp 204–205° C; MS (ES$^+$) m/e 418[MH]$^+$.

Example 10

3-(3-Methyl-1,2 4-oxadiazol-5-yl)-6-(2-quinolino)methyloxy-7,8,9,10-tetrahydro-(7,10-ethano)-1,2,4-triazolo [3,4-a]phthalazine a) 2-(Hydroxymethyl)quinoline A mixture of 2-(chloromethyl)quinoline hydrochloride (1.50 g, 7.00 mmol) and sodium acetate trihydrate (2.86 g, 21.0 mmol) in DMF (40 ml) was heated at 100° C. under nitrogen for 6 h. The reaction mixture was poured into ether, washed with water (×3), dried (MgSO$_4$) and evaporated in vacuo. The residue was dissolved in methanol/water (9:1) (40 ml), sodium hydroxide (0.50 g, 12.5 mmol) added and the mixture heated at reflux for 0.75 h. The solvent was evaporated in vacuo and the residue partitioned between dichloromethane and water. The organic layer was separated, washed with water (×1), dried (MgSO$_4$) and evaporated in vacuo. The residue was flash chromatographed on silica gel, eluting with 4:1 ethyl acetate/hexane, to give the title-alcohol (0.85 g, 76%); $^1$H NMR (250 MHz, CDCl$_3$) δ4.51 (1H, br s, OH), 4.93 (2H, s, CH$_2$), 7.29 (1H, d, J=8.5 Hz, Ar—H), 7.55 (1H, t, J=6.9 Hz, Ar—H), 7.73 (1H, m, Ar—H), 7.84 (1H, dd, J=8 and 1.3 Hz, Ar—H), 8.09 (1H, d, J=8.4 Hz, Ar—H), 8.14 (1H, d, J=8.5 Hz, Ar—H).

b) 3-(3-Methyl-1,2,4-oxadiazol-5-yl)-6-(2-quinolino)methyloxy-7,8,9,10-tetrahydro-(7,10-ethano)-1,2,4-triazolo[3,4-a]phthalazine The title-compound was prepared from Intermediate 1 and the preceding alcohol using the procedure given for Example 7, mp 216–218° C.; $^1$H NMR (360 MHz, CDCl$_3$) δ1.43–1.55 (4H, m, 2 of CH$_2$), 1.92–2.02 (4H, m, 2 of CH$_2$), 2.59 (3H, s, Me), 3.65 (1H, br s, CH), 4.03 (1H, br s, CH), 5.84 (2H, s, CH$_2$), 7.58 (1H, t, J=7.6 Hz, Ar—H), 7.73–7.86 (2H, m, 3 of Ar—H), 8.11 (1H, d, J=8.6 Hz, Ar—H), 8.24 (1H, d, J=8.3 Hz, Ar—H): MS (ES$^+$) m/e 440 [MH]$^+$; Anal. Found C, 64.81; H, 4.51; N, 21.74. C$_{24}$H$_{21}$N$_7$O$_2$.0.3H$_2$O requires C, 64.79; H, 4.89; N, 22.04%.

Example 11

3-(3-Methyl-1,2,4-oxadiazol-5-yl)-6-(2-pyridyl-N-oxide)methyloxy-7,8,9,10-tetrahydro-(7,10-ethano)-1,2,4-triazolo[3,4-a]phthalazine m-Chloroperbenzoic acid (62 mg of a 55% purity sample, 0.20 mmol) was added to a stirred solution of 3-(3-methyl-1,2,4-oxadiazol-5-yl)-6-(2-pyridyl)methyloxy-7,8,9,10-tetrahydro-(7,10-ethano)-1,2,4-triazolo[3,4-a]phthalazine (43 mg, 0.1 mmol) in dichloromethane (3 ml) at room temperature under nitrogen. After stirring for 17 h, the mixture was diluted with dichloromethane, washed with saturated potassium carbonate solution (×2) and water (×1), dried (MgSO$_4$) and evaporated in vacuo. The residue was chromatographed on silica gel, eluting with 5% methanol/dichloromethane, and then recrystallised (ethyl acetate/hexane) to give the title-product (21 mg, 47%), mp 225–227° C.; $^1$H NMR (360 MHz, CDCl$_3$) δ1.42–1.54 (4H, m, 2 of CH$_2$), 1.92–2.02 (4H, m, 2 of CH$_2$), 2.60 (3H, s, Me), 3.62 (1H, br s, CH), 4.03 (1H, br s, CH), 5.85 (2H, s, CH$_2$), 7.31–7.33 (2H, m, 2 of Ar—H), 7.86 (1H, m, Ar—H), 8.33 (1H, m, Ar—H): MS (ES$^+$) m/e 406 [MH]+; Anal. Found C, 56.54; H, 4.69; N, 22.91. C$_{20}$H$_{19}$N$_7$O$_3$.H$_2$O requires C, 56.73; H, 4.99; N, 23.15%.

Example 12

6-(2-Imidazolyl)methyloxy-3-(3-methyl-1,2,4-oxadiazol-5-yl)-7,8,9,10-tetrahydro-(7,10-ethano)-1,2,4-triazolol[3,4-a]phthalazine a) 2-(Hydroxymethyl)-1-{[2-(trimethylsilyl)ethoxyl]methyl}-imidazole Sodium borohydride (0.42 g, mmol) was added to a stirred solution of 1-{([2-(trimethylsilyl)ethoxy]methyl}-1H-imidazole-2-carboxaldehyde (7.45 g, 33 mmol) (prepared as described in *J. Org. Chem.*, 1986, 51, 1891) in methanol (30 ml) at 0° C. The solution was stirred at 0° C. for 0.67 h, brine (15 ml) added and the mixture stirred at room temperature for 0.25 h. The methanol was evaporated in vacuo and the aqueous solution washed with ethyl acetate (3×50 ml). The combined organic layers were dried (Na$_2$SO$_4$) and evaporated in vacuo to yield an oil which crystallised at 0° C. The solid was washed and recrystallised (hexane) to give the title-imidazole as colourless crystals (1.99 g, 26%); $^1$H NMR (250 MHz, CDCl$_3$) δ0.00 (9H, s, SiMe$_3$), 0.93 (2H, t, J=8.2 Hz, CH$_2$), 3.54 (2H, t, J=8.2 Hz, CH$_2$), 4.73 (2H, s, CH$_2$), 4.77 (1H, br s, OH), 5.39 (2H, s, CH$_2$), 6.94 (1H, d, J=1.4 Hz, Ar—H), 7.00 (1H, d, J=1.4 Hz, Ar—H); MS (ES$^+$) m/e 229 [MH]$^-$.

b) 3-(3-Methyl-1,2,4-oxadiazol-5-yl)-6-[2-{1-[2-(trimethylsilyl)ethoxy]methyl}imidazolyl]methyloxy-7,8,9,10-tetrahydro-(7,10-ethano)-1,2,4-triazolo[3,4-a]phthalazine The title-compound was prepared from Intermediate 1 and the preceding alcohol using the procedure given for Example 7, $^1$H NMR (360 MHz, CDCl$_3$) δ0.00 (9H, s, SiMe$_3$), 0.91 (2H, t, J=8.1 Hz, CH$_2$), 1.40–1.56 (4H, m, 2 of CH$_2$), 1.89–2.02 (4H, m, 2 of CH$_2$), 2.62 (3H, s, Me), 3.53–3.58 (3H, m, CH and CH$_2$), 4.05 (1H, br s, CH), 5.50 (2H, s, CH$_2$), 5.72 (2H, s, CH$_2$), 7.14 (1H, d, J=1.4 Hz, Ar—H), 7.16 (1H, d, J=1.4 Hz, Ar—H); MS (ES$^+$) m/e 509 [MH]$^+$.

c) 6-(2-Imidazolyl)methyloxy-3-(3-methyl-1,2,4-oxadiazol-5-yl)-7,8,9,10-tetrahydro-(7,10-ethano)-1,2,40-triazolo[3,4-a]phthalazine A stirred solution of the preceding product (355 mg, 0.698 mmol) in 5N HCl (14 ml) was heated at 40° C. for 2.3 h. Ethanol was added and the mixture evaporated in vacuo. The residue was azeotroped with ethanol (×2), partitioned between dichloromethane and water and basified with saturated potassium carbonate solution. The organic layer was separated and the aqueous phase re-extracted with dichloromethane (×1). The combined organic extracts were washed with water (×1), dried (MgSO$_4$) and evaporated in vacuo, and the residue recrystallised (ethyl acetate-hexane) to give the title-compound (190 mg, 72%), mp 187° C.; $^1$H NMR (360 MHz, CDCl$_3$) δ1.36–1.50 (4H, m, 2 of CH$_2$), 1.88–2.00 (4H, m, 2 of CH$_2$), 2.66 (3H, s, Me), 3.56 (1H, br s, CH), 4.01 (1H, br s, CH), 5.58 (1H, br s, CH$_2$), 7.10 (2H, s, 2 of Ar—H); MS (ES$^+$) m/e 379 [MH]$^+$; Anal. Found C, 57.30; H, 4.84; N, 29.14. C$_{18}$H$_{18}$N$_8$O$_2$. 0.05H$_2$O requires C, 57.00; H, 4.81; N, 29.54%.

Example 13

6-[2-(1-Methyl)imidazoyl]methyloxy-3-(3-methyl-1,2,4-oxadiazol-5-yl)-7,8,9,10-tetrahydro-(7,10-ethano)-1,2,4-triazolo[3,4-a]phthalazine The title-compound was prepared from Intermediate 1 and 1-methyl-2-(hydroxymethyl)imidazole using the procedure given for Example 7, mp 215–216° C.; $^1$H NMR (360 MHz, CDCl$_3$) δ1.36–1.53 (4H, m, 2 of CH$_2$), 1.86–1.99 (4H, m, 2 of CH$_2$), 2.58 (3H, s, M), 3.50 (1H, br S, CH 3.80 (3H, s, Me), 4.02 (1H, br s, CH), 5.65 (2H, s, CH$_2$), 6.98 (1H, d, J=1.1 Hz, Ar—H), 7.10 (1H, d, J=1.4 Hz, Ar—H); MS (ES$^+$) m/e 393 [MH]$^+$; Anal. Found C, 57.91; H, 5.02; N, 28.07. C$_{19}$H$_{20}$N$_8$O$_2$.0.2H$_2$O requires C, 57.62; H. 5.19; N, 28.29%.

Example 14

6-[2-(Cyano)phenyl]methyloxy-3-(3-methyl-1,2,4-oxadiazol-5-yl)-7,8,9,10-tetrahydro-(7,10-ethano)-1,2,4-triazolo[3,4-a]phthalazine a) 2-Cyanobenzyl Alcohol

Sodium borohydride (0.87 g, 23.0 mmol) was added to a stirred suspension of 2-cyanobenzaldehyde (3.00 g, 22.9 mmol) in ethanol (20 ml) at 0° C. under nitrogen. The mixture was stirred at room temperature for 0.8 h and the solvent then evaporated in vacuo. The residue was partitioned between dichloromethane (60 ml) and water (60 ml) and the aqueous layer separated and re-extracted with dichloromethane (60 ml). The combined organic extracts were dried (MgSO$_4$) and evaporated in vacuo, and the residue chromatographed on silica gel, eluting with 5% methanol/dichloromethane, to give the title-alcohol (1.71 g, 56%), $^1$H NMR (250 MHz, CDCl$_3$) δ5.32 (2H, s, CH$_2$), 7.39–7.66 (3H, m, 3 of Ar—H), 7.88 (1H, d, J=7.5 Hz, Ar—H).

b) 6-[2-(Cyano)phenyl]methyloxy-3-(3-methyl-1,2,4-oxadiazol-5-yl)-7,8,9,10-tetrahydro-(7,10-ethano)-1,2,4-triazolo[3,4-a]phthalazine The title-compound was prepared from Intermediate 1 and the preceding alcohol using the procedure given for Example 7, mp197–198° C.; $^1$H NMR (360 MHz, CDCl$_3$) δ1.42–1.53 (4H, m, 2 of CH$_2$), 1.90–1.99 (4H, m, 2 of CH$_2$), 2.62 (3H, s, Me), 3.60 (1H, br s, CH), 4.01 (1H, br s, CH), 5.73 (2H, s, CH$_2$), 7.49 (1H, t, J=7.6 Hz, Ar—H), 7.64 (1H, dt, J=1.1 and 7.6 Hz, Ar—H) 7.76 (1H, d, J=7.6 Hz, Ar—H), 7.87 (1H, d, J=7.6 Hz, Ar—H); MS (ES$^+$) m/e 414 [MH]$^+$; Anal. Found C, 63.62; H. 4.40; N, 23.38. C$_{22}$H$_{19}$N$_7$O$_2$ requires C. 63.91; H, 4.63; N, 23.72%.

Example 15

6-(2-Bromophenyl)methyloxy-3-(3-methyl-1,2,4-oxadiazol-5-yl)-7,8,9,10-tetrahydro-(7,10-ethano)-1,2,4-triazolo[3,4-a]phthalazine The title-compound was prepared from Intermediate 1 and 2-bromobenzyl alcohol using the procedure given for Example 7. mp 217–218° C.; $^1$H NMR (360 MHz, CDCl$_3$) δ1.38–1.53 (4H, m, 2 of CH$_2$), 1.88–1.99 (4H, m, 2 of CH$_2$), 2.61 (3H, s, Me), 3.57 (1H, br s, CH),4.01 (1H, br s, CH), 5.63 (2H, s, CH$_2$), 7.25 (1H, dt, J=1.8 and 7.6 Hz, Ar—H), 7.35 (1H, m, Ar—H), 7.64 (1H, dd, J=1.1 and 7.9 Hz, Ar—H), 7.74 (1H, dd, J=1.4 and 7.6 Hz, Ar—H); MS (ES$^+$) m/e 467 [MH]$^+$.

Example 16

3-(3-Methyl-1,2,4-oxadiazol-5-yl)-6-(4-thiazolo)methyloxy-7,8,9,10-tetrahydro-(7,10-ethano)-1,2,4-triazolo[3,4-a]phthalazine The title-compound was prepared from Intermediate 1 and 4-hydroxymethylthiazole (prepared in an analogous manner to that described in *J. Am. Chem. Soc.*, 1954, 76, 1286) using the procedure given for Example 8, mp 119–121° C.; MS (ES$^+$) m/e 418 [MH]$^+$.

Example 17

3-(3-Methyl-1,2,4-oxadiazol-5-yl)-6-(N-pyrrolidinylcarbonyl)methyloxy-7,8,9,10-tetrahydro-(7,10-ethano)-1,2,4-triazolo[3,4-a]phthalazine a) N-Hydroxymethylcarbonylpyrrolidine

A stirred solution of methyl glycolate (2.0 g, 22.2 mmol) in pyrrolidine (16.0 g, 225 mmol) was heated at 90° C. for 3 h. The pyrrolidine was removed by distillation and the residue partitioned between dichloromethane (150 ml) and 2N HCl (30 ml). The aqueous layer was separated and re-extracted with dichloromethane (×2). The combined organic layers were dried (Na$_2$SO$_4$) and evaporated in vacuo to afford the title-pyrrolidine (2.0 g, 70%); $^1$H NMR (250 MHz, CDCl$_3$) δ1.84–2.05 (4H, m, 2 of CH$_2$), 2.95 (1H, br s, OH), 3.28 (2H, t, J=6.8 Hz, CH$_2$N), 3.55 (2H, t, J=6.8 Hz, CH$_2$N), 4.08 (2H, CH$_2$O).

b) 3-(3-Methyl-1,2,4-oxadiazol-5-yl)-6-(N-pyrrolidinylcarbonyl)methyloxy-7,8,9,10-tetrahydro-(7,10-ethano)-1,2,4-triazolo[3,4-a]phthalazine The title-compound was prepared from Intermediate 1 and the preceding alcohol using the procedure given for Example 7. mp 234–235° C.: $^1$H NMR (360 MHz, CDCl$_3$) δ1.48–1.50 (4H, m, 2 of CH$_2$), 1.89–1.99 (6H, m, 3 of CH$_2$), 2.09–2.16 (2H, quintet, J=6.8 Hz, CH$_2$), 2.55 (3H, s, Me), 3.51 (2H, t, J=6.8 Hz, CH$_2$N), 3.64–3.67 (3H, m, CH$_2$N and CH), 4.01 (1H, br s, CH), 5.09 (2H, s, CH$_2$O); MS (ES$^+$) m/e 410 [MH]$^+$; Anal. Found C, 58.47; H, 5.72; N, 23.47. C$_{20}$H$_{23}$N$_7$O$_3$. 0.15 H$_2$O requires C, 58.28; H, 5.70; N, 23.79%.

Example 18

3-(3-Ethyl-1,2,4-oxadiazol-5-yl)-6-(6-methylpyridin-2-yl)methyloxy-7,8,9,10-tetrahydro-(7,10-ethano)-1,2,4-triazolo[3,4-a]phthalazine The title-compound was prepared from propionamide oxime using the procedure described for Example 5, mp 169–171° C.; $^1$H NMR (360 MHz, CDCl$_3$) δ1.40–1.54 (7H, m, 2 of CH$_2$ and Me), 1.90–2.00 (4H, m, 2 of CH$_2$), 2.60 (3H, s, Me), 2.97 (2H, q, J=7.6 Hz, CH$_2$), 3.61 (1H, br s, CH), 4.01 (1H, br s, CH), 5.62 (2H, s, CH$_2$), 7.14 (1H, d, J=7.9 Hz, Ar—H), 7.49 (1H, d, J=7.6 Hz, Ar—H), 7.64 (1H, t, J=7.6 Hz, Ar—H); MS (ES$^+$) m/e 418 [MH]$^+$; Anal Found C, 63.28; H, 23.49; N, 23.24. C$_{22}$H$_{23}$N$_7$O$_2$ requires C, 63.29; H, 5.55; N, 23.49%.

Example 19

3-(3-Isopropyl-1,2,4-oxadiazol-5-yl)-6-(6-methylpyridin-2yl)methyloxy-7,8,9,10-tetrahydro-(7,10-ethano)-1,2,4-triazolo[3,4-a]phthalazine The title-compound was prepared from 2-methylpropionamide oxime using the procedure described for Example 5, mp 185–187° C.; $^1$H NMR (360 MHz, CDCl$_3$) δ1.40–1.52 (10H, m, 2 of CH$_2$ and CHMe$_2$), 1.88–2.00 (4H, m, 2 of CH$_2$), 2.60 (3H, s, Me), 3.30 (1H, septet, J=6.8 Hz, CHMe$_2$), 3.61 (1H, br s, CH), 4.01 (1H, br s, CH), 5.62 (2H, s, CH$_2$), 7.14 (1H, d, J=7.6 Hz, Ar—H), 7.50 (1H, d, J=7.6 Hz, Ar—H), 7.63 (1H, t, J=7.8 Hz, Ar—H); MS (ES$^+$) m/e 432 [MH]$^+$; Anal. Found C, 63.68; H, 5.45; N, 22.38. C$_{23}$H$_{25}$N$_7$O$_2$ requires C, 64.02; H, 5.84; N, 22.72%.

Example 20

6-(6-Methylpyridin-2-yl)methyloxy-3-[3-(piyridin-3-yl)-1,2,4-oxadiazol-5-yl]-7,8,9,10-tetrahydro-(7,10-ethano)-1,2,4-triazolo[3,4-a]phthalazine a) 3-Pyridylcarboxamide Oxime

A solution of 3-cyanopyridine (10.0 g, 96 mmol) in ethanol (100 ml) was added to a stirred solution of hydroxylamine hydrochloride (13.3 g, 192 mmol) and potassium carbonate (15.9 g, 120 mmol) in ethanol (150 ml). The mixture was heated at reflux for 16 h, then added to room temperature, filtered through a pad of Celite and evaporated in vacuo to give the title-oxime, $^1$H NMR (360 MHz, d$^6$-DMSO) 5.97 (2H, br s), 7.40 (0.56H, m), 7.50 (0.45H, m), 8.02 (0.5H, m), 8.20 (0.5H, m), 8.56 (0.55H, m), 8.70 (0.45H, m), 8.86 (0.55H, m), 9.04 (0.45H, m), 9.77 (1H, br s).

b) Ethyl-[3-(Pyridin-3-yl)-1,2,4-oxadiazol-5-yl] carboxylate

A mixture of the preceding amide oxime (3.0 g, 22 mmol) and 4 Å molecular sieves in THF (120 ml) was stirred vigorously at room temperature under nitrogen. Sodium hydride (0.96 g of a 60% dispersion in oil, 24 mmol) was added, the mixture stirred for 0.1 h and then ethyl oxalyl chloride (3.0 g, 22 mmol) added. The mixture was heated at reflux for 1 h, cooled to room temperature and filtered through celite. The solvent was evaporated in vacuo and the residue dissolved in dichloromethane, washed with water (×2), dried (MgSO$_4$) and evaporated in vacuo. The residue was chromatographed on silica gel, eluting with ethyl acetate:hexane (1:1) to give the title-product (1.30 g, 28%), $^1$H NMR (360 MHz, CDCl$_3$) 1.51 (3H, t, J=7.0 Hz, Me), 4.59 (2H, q, J=7.1 Hz, CH$_2$), 7.47 (1H, m, Ar—H), 8.43 (1H, m, Ar—H), 8.78 (1H, m, Ar—H), 9.39 (1H, m, Ar—H).

c) 6-(6-Methylpyridin-2-yl)methyloxy-3-[3-(pyridin-3-yl)-1,2,4-oxadiazol-5-yl]-7,8,9,10-tetrahydro-(7,10-ethano)-1,2,4-triazolo[3,4-a]phthalazine The title-compound was prepared from the preceding ester using the procedure described for Example 5, steps b-c, mp 202–204° C.; $^1$H NMR (250 MHz, CDCl$_3$) δ1.42–1.58 (4H, m, 2 of CH$_2$), 1.90–2.08 (4H, m, 2 of CH$_2$), 2.61 (3H, s, Me), 3.64 (1H, br s, CH), 4.05 (1H, br s, CH), 5.67 (2H, s, CH$_2$), 7.16 (1H, d, J=7.5 Hz, Ar—H), 7.49–7.52 (2H, m, Ar—H), 7.65 (1H, t, J=7.6 Hz, Ar—H), 8.56 (1H, m, Ar—H), 8.80 (1H, m, Ar—H), 9.51 (1H, br s, Ar—H); MS (ES$^+$) m/e 467 [MH]$^+$; Anal. Found C, 55.05; H, 5.18; N, 20.45. C$_{25}$H$_{22}$N$_8$O$_2$.1,2H$_2$O.1.5HCl requires C, 55.31; H, 4.81; N, 20.64%.

Example 21

6-(6-Methylpyridin-2-yl)methyloxy-3-[3-(pyridin-4-yl)-1,2,4-oxadiazol-5-yl]-7,8,9,10-tetrahydro-(7,10-ethano)-1,2,4-triazolo[3,4-a]phthalazine The title-compound was prepared from 4-cyanopyridine using the procedure described for Example 20, mp 272–274° C.; $^1$H NMR (250 MHz, CDCl$_3$) δ1.42–1.58 (4H, m, 2 of CH$_2$), 1.90–2.05 (4H, m, 2 of CH$_2$), 2.61 (3H, s, Me), 3.64 (1H, br s, CH), 4.05 (1H, br s, CH), 5.67 (2H, s, CH$_2$), 7.16 (1H, d, J=7.8 Hz, Ar—H), 7.49 (1H, d, J=7.8 Hz, Ar—H), 7.64 (1H, d, J=7.7 Hz, Ar—H), 8.13–8.16 (2H, m, Ar—H), 8.84–8.86 (2H, m, Ar—H); MS (ES$^+$) m/e 467 [MH]$^+$; Anal. Found C, 64.80; H, 4.56; N, 23.62. C$_{25}$H$_{22}$N$_8$O$_2$.0.1 (CH$_2$Cl$_2$) requires C, 64.37; H, 4.56; N, 24.02%.

Example 22

6-(5,6-Dimethylpyridin-2-yl)methyloxy-3-[3-(pyridin-3-yl)-1,2,4-oxadiazol-5-yl]-7,8,9,10-tetrahydro-(7,10-ethano)-1,2,4-triazolo[3 4-a]phthalazine The title-compound was prepared from ethyl-[3-(pyridin-3-yl)-1,2,4-oxadiazol-5-yl]carboxylate, 3-chloro-6-hydrazino-4,5-diazatricyclo[6.2.2]dodeca-2(7),3,5-triene and 2-hydroxymethyl-5,6-dimethylpyridine using the procedure described for Example 5 step b and Example 9, mp 215–216° C.; $^1$H NMR (360 MHz, CDCl$_3$) δ1.42–1.54 (4H, m, 2 of CH$_2$), 1.89–2.02 (4H, m, 2 of CH$_2$), 2.30 (3H, s, Me), 2.53 (3H, s, Me), 3.62 (1H, br s, CH), 4.03 (1H, br s, CH), 5.63 (2H, s, CH$_2$), 7.42–7.51 (3H, im, 3 of Ar—H), 8.56 (1H, m, Ar—H), 8.80 (1H, m, Ar—H), 9.51 (1H, br s, Ar—H); MS (ES$^+$) m/e 481 [MH]$^+$; Anal. Found C, 65.14; H, 4.75; N, 23.12. C$_{26}$H$_{24}$N$_8$O$_2$ requires C, 64.99; H, 5.03; N, 23.32%.

Example 23

3-(2-Methyloxazol-4-yl)-6-(2-pyridyl)methyloxy-7,8,9,10-tetrahydro-(7,10-ethano)-1,2,4-triazolo[3,4-a]phthalazine a) Ethyl(2-methyl-2-oxazolin-4-yl)carboxylate

Triethylamine (8.2 ml, 59 mmol) was added to a stirred mixture of L-serine ethyl ester hydrochloride (5.00 g, 29.5 mmol) and ethyl acetimidate hydrochloride (3.64 g, 29.5 mmol) in dichloromethane (150 ml) at 0° C. under nitrogen. The mixture was stirred at 0° C. for 1.25 h and at room temperature for 19 h and then partitioned between dichloromethane and water. The organic layer was separated, washed with water (×3), dried (MgSO$_4$) and evaporated in vacuo and the residue chromatographed on silica gel, eluting with diethyl ether, to give the title-ester (2.68 g, 37%), $^1$H NMR (360 MHz, CDCl$_3$) δ1.31 (3H, t, J=7 Hz, Me), 2.04 (3H, s, Me), 4.16–4.51 (4H, m, 2 of CH$_2$), 4.70 (1H, m, CH); MS (ES$^+$) m/e 158 [MH]$^+$.

b) Ethyl (2-methyloxazol-4-yl)carboxylate

A stirred mixture of the preceding compound (2.18 g, 13.9 mmol) and N-bromosuccinimide (3.70 g, 20.8 mmol) in dichloromethane (90 ml) at −15° C. under nitrogen was irradiated for 7 h. A second portion of N-bromosuccinimide (0.45 g, 2.5 mmol) was added and the mixture irradiated for a further 4 h. The reaction mixture was filtered and the filtrate diluted with dichloromethane, washed with water (×3), dried (MgSO$_4$) and evaporated in vacuo. The residue was chromatographed on silica gel, eluting with diethyl ether/hexane (70:30), to give the title-ester (0.95 g, 44%), $^1$H NMR (250 MHz, CDCl$_3$) δ1.38 (3H, t, J=7.3 Hz, Me), 2.52 (3H, s, Me), 4.39 (2H, J=7 Hz, CH$_2$), 8.13 (1H, s, Ar—H); MS (ES$^+$) m/e 156 [MH]$^+$.

c) 2-Methyloxazole-4-carboxylic Acid

A solution of sodium hydroxide (0.97 g, 24 mmol) in water (10 ml) was added to a stirred solution of the preceding ester (0.94 g, 6.1 mmol) in methanol (6 ml). After 1.25 h at room temperature, the methanol was evaporated in vacuo and the aqueous solution cooled to 0–5° C. and acidified to pH 1 with 5N HCl. Ethanol was added, the solvents evaporated in vacuo and the residue azeotroped with ethanol. The resulting solid was mixed with ethanol, filtered and evaporated in vacuo. The process was repeated to give the title-acid (0.776 g, 100%), 1H NMR (360 MHz, d$^6$-DMSO) δ2.44 (3H, s, Me), 8.60 (1H, s, Ar—H); MS (ES$^+$) m/e 128 [MH]$^+$.

d) 6-Chloro-3-(2-methyloxazol-4-yl)-7,8,9,10-tetrahydro-(7,10-ethano)-1,2,4-triazolo[3,4-a]phthalazine 1,1'-Carbonyldiimidazole (1.011 g, 6.23 mmol) was added to a stirred solution of the preceding acid (0.755 g, 5.94 mmol) in DMF (20 ml) at room temperature under nitrogen. The solution was stirred for 1.1 h before adding 3-chloro-6-hydrazino-4,5-diazatricyclo[6.2.2.2.7]dodeca-2 (7),3,5-triene (1.335 g, 5.94 mmol). After 2.5 h, the solvent was evaporated in vacuo and the residue triturated with water. The solid was filtered off, washed with water and hexane, and dried in vacuo to give the ketohydrazine (1.645 g, 83%), MS (ES$^+$) m/e 334 [MH]$^+$. A solution of the ketohydrazine (1.855 g, 5.56 mmol) and triethylamine hydrochloride (0.186 g, 0.556 mmol) in xylene (28 ml) was heated at reflux for 3 h. The solution was cooled to room temperature and the solvent evaporated in vacuo. The residue was dissolved in dichloromethane, washed with water (×3), dried (MgSO$_4$) and evaporated in vacuo, and the crude product was chromatographed on silica gel, eluting with 7% methanol/dichloromethane, to give the title-phthalazine (0.917 g, 52%), $^1$H NMR (250 MHz, CDCl$_3$) δ1.42–1.56 (4H, m, 2 of CH$_2$), 1.92–2.04 (4H, m, 2 of CH$_2$), 2.62 (3H, s, Me), 3.58 (1H, br s, CH), 4.09 (1H, br s, CH), 8.59 (1H, s, Ar—H); MS (ES$^+$) m/e 316 [MH]$^+$.

e) 3-(2-Methyloxazol-4-yl)-6-(2-pyridyl)methyloxy-7,8,9,10-tetrahydro-(7,10-ethano)-1,2,4-triazolo[3,4-a]phthalazine The title-compound was prepared from the preceding phthalazine and 2-pyridylcarbinol using the procedure given for Example 7, mp 222–224° C.; $^1$H NMR (360 MHz, CDCl$_3$) 1.42–1.53 (4H, m, 2 of CH$_2$), 1.90–1.98 (4H, m, 2 of CH$_2$), 2.59 (3H, s, Me), 3.59 (1H, br s, CH), 4.00 (1H, br s, CH), 5.62 (2H, s, CH$_2$), 7.30 (1H, m, Ar—H), 7.51 (1H, d, J=7.9 Hz, Ar—H), 7.76 (1H, m, Ar—H), 8.47 (1H, s, Ar—H), 8.68 (1H, m, Ar—H); MS (ES$^+$) m/e 389 [MH]$^+$; Anal. Found C, 65.04; H, 5.11; N, 21.33. C$_{21}$H$_{20}$N$_6$O$_2$ requires C, 64.94; H, 5.19; N, 21.64%.

Example 24

3-(2-Methyloxazol-4-yl)-6-(6-methylpyridin-2-yl)methyloxy-7,8,9,10-tetrahydro-(7,10-ethano)-1,2,4-triazolo[3,4-a]phthalazine The title-compound was prepared from 6-chloro-3-(2-methyloxazol-4-yl)-7,8,9,10-tetrahydro-(7,10-ethano)-1,2,4-triazolo[3,4-a]phthalazine and 6-methyl-2-pyridylcarbinol using the procedure given for Example 7, mp 195–197° C.; 360 MHz ($^1$H NMR, CDCl$_3$) δ1.42–1.54 (4H, m, 2 of CH$_2$), 1.90–1.98 (4H, m, 2 of CH$_2$), 2.59 (3H, s, Me), 2.64 (3H, s, Me), 3.58 (1H, br s, CH), 4.00 (1H, br s, CH), 5.60 (2H, s, CH$_2$), 7.15 (1H, d, J=7.6 Hz, Ar—H), 7.32 (1H, d, J=7.6 Hz, Ar—H), 7.65 (1H, t, J=7.6 Hz, Ar—H), 8.56 (1H, s, Ar—H); MS (ES$^+$) m/e 403 [MH]$^+$; Anal. Found. C, 65.36; H, 5.51; N, 21.02. C$_{22}$H$_{22}$N$_6$O$_2$ requires C, 65.66; H, 5.51; N, 20.88%.

Example 25

3-(5-Methylisoxazol-3-yl)-6-(2-pyridyl)methyloxy-7,8,9,10-tetrahydro-(7,10-ethano)-1,2,4-triazolo[3,4-a]phthalazine The title-compound was prepared from 6-chloro-3-(5-methylisoxazol-3-yl)-7,8,9,10-tetrahydro-(7,10-ethano)-1,2,4-triazolo[3,4-a]phthalazine and 2-pyridylcarbinol using the procedure given for Example 1, part b, $^1$H NMR (360 MHz, CDCl$_3$) δ1.40–1.52 (4H, m, 2 of CH$_2$), 1.86–1.98 (4H, m, 2 of CH$_2$), 2.57 (3H, s, Me), 3.58 (1H, br s, CH), 3.98 (1H, br s, CH), 5.63 (2H, s, CH$_2$), 6.83 (1H, s, Ar—H), 7.29 (1H, m, Ar—H), 7.68 (1H, d, J=7.7 Hz, Ar—H), 7.76 (1H, m, Ar—H), 8.66 (1H, m, Ar—H); MS (ES$^+$) m/e 389 [MH]$^+$.

Example 26

3-(5-Methylisoxazol-3-yl)-6-(2-cyanophenyl)methyloxy-7,8,9,10-tetrahydro-(7,10-ethano)-1,2,4-triazolo[3,4-a]phthalazine The title-compound was prepared from 6-chloro-3-(5-methylisoxazol-3-yl)-7,8,9,10-tetrahydro-(7,10-ethano)-1,2,4-triazolo[3,4-a]phthalazine and 2-cyanobenzyl alcohol using the procedure given for Example 1. part b, $^1$H NMR (250 MHz, CDCl$_3$) δ1.38–1.52 (4H, m, 2 of CH$_2$), 1.84–1.98 (4H, m, 2 of CH$_2$), 2.59 (3H, s, Me), 3.55 (1H, br s, CH), 3.97 (1H, br s, CH), 5.70 (2H, s, CH$_2$), 6.85 (1H, s, Ar—H), 7.49 (1H, m, Ar—H), 7.65 (1H, m, Ar—H), 7.75 (1H, d, J=7.6 Hz, Ar—H), 7.89 (1H, d, J=7.1 Hz, Ar—H); MS (ES$^+$) m/e 413 [MH]$^+$; Anal. Found C, 64.52; H, 4.90; N, 19.40. C$_{23}$H$_{20}$N$_6$O$_2$.0.9H$_2$O requires C, 64.44; H, 5.13; N, 19.61%.

Example 27

6-(3-Methylpyridin-2-yl)methyloxy-3-(2-pyrazinyl)-7,8,9,10-tetrahydro-(7,10-ethano)-1,2,4-triazolo[3,4-a]phthalazine The title-compound was prepared from 6-chloro-3-(2-pyrazinyl)-7,8,9,10-tetrahydro-(7,10-ethano)-1,2,4-triazolo

[3,4-a]phthalazine and 3-methyl-2-pyridylcarbinol using the procedure given for Example 1, part b, $^1$H NMR (360 MHz, CDCl$_3$) δ1.38–1.54 (4H, m, 2 of CH$_2$), 1.85–1.98 (4H, m, 2 of CH$_2$), 2.44 (3H, s, Me), 3.50 (1H, br s, CH), 4.02 (1H, br s, CH), 5.64 (2H, s, CH$_2$), 7.24 (1H, m, Ar—H), 7.57 (1H, d, J=7.4 Hz, Ar—H), 8.49 (1H, m, Ar—H), 8.68 (1H, m, Ar—H), 8.82 (1H, m, Ar—H), 9.74 (1H, d, J=1.5 Hz, Ar—H); MS (ES$^+$) m/e 400 [MH]$^+$; Anal. Found C, 66.39; H, 5.36; N, 24.53. C$_{22}$H$_{21}$N$_7$O$_2$ requires C, 66.15; H, 5.30; N, 24.55%.

Example 28

3-(2-Pyrazinyl)-6-(2-pyridyl)methyloxy-7,8,9,10-tetrahydro-(7,10-ethano)-1,2,4-triazolo[3,4-a]phthalazine The title-compound was prepared from 6-chloro-3-(2-pyrazinyl)-7,8,9,10-tetrahydro-(7,10-ethano)-1,2,4-triazolo[3,4-a]phthalazine and 2-pyridylcarbinol using the procedure given for Example 1, part b, $^1$H NMR (250 MHz, CDCl$_3$) δ1.41–1.57 (4H, m, 2 of CH$_2$), 1.89–2.02 (4H, m, 2 of CH$_2$), 3.60 (1H, br s, CH), 4.03 (1H, br s, CH), 5.63 (2H, s, CH$_2$), 7.29 (1H, m, Ar—H), 7.59 (1H, d, J=7.8 Hz, Ar—H), 7.87 (1H, td, J=7.7 and 1.7 Hz, Ar—H), 8.66–8.70 (2H, m, Ar—H), 8.83 (1H, m, Ar—H), 9.65 (1H, d, J=1.2 Hz, Ar—H); MS (ES$^+$) m/e 386 [MH]$^+$; Anal. Found C, 64.34; H, 4.99; N, 24.74. C$_{21}$H$_{19}$N$_7$O.0.5H$_2$O requires C, 63.95; H, 5.11; N, 24.86%.

Example 29

3-(5-Methylisoxazol-3-yl)-6-(2-pyridyl)methyloxy-7,8,9,10-tetrahydro-(7,10-methano)-1,2,4-triazolo[3,4-a]phthalazine a) 3-Chloro-6-hydrazino-4,5-diazatricyclo[6.2.1,2,7]undeca-2(7),3,5-triene Prepared using the procedures described for Reference Example 1, steps a–c, with 2-norbornene-2,3-dicarboxylic anhydride being used instead of bicyclo[2.2.2.]oct-2-ene-2,3-dicarboxylic acid anhydride in step a, $^1$H NMR (250 MHz, CDCl$_3$) δ1.10–1,24 (2H, m, CH$_2$), 1.58 (1H, m, CH$_2$), 1.80 (1H, m, CH$_2$), 1.96–2.10 (2H, m, CH$_2$), 3.49 (1H, d, J=1.8 Hz, CH), 3.55 (1H, d, J=1.6 Hz, CH).

b) 3-(5-Methylisoxazol-3-yl)-6-(2-pyridyl)methyloxy-7,8,9,10-tetrahydro-(7,10-methano)-1,2,4-triazolo[3,4-a]phthalazine The preceding hydrazine was coupled with 5-methylisoxazole-3-carboxylic acid using the procedure described for Example 1, part a. The resultant triazolopyridazine was reacted with 2-pyridylcarbinol using the procedure given for Example 1, part b, to afford the title-compound, $^1$H NMR (360 MHz, CDCl$_3$) δ1.22–1.34 (2H, m, CH$_2$), 1.69 (1H, d, J=9.2 Hz, CH$_2$), 1.95 (1H, d, J=9.2 Hz, CH$_2$), 2.05–2.16 (2H, m, CH$_2$), 3.76 (1H, br s, CH), 4.13 (1H, br s, CH), 5.62 (1H, d, J=13.1 Hz, CH$_2$), 5.66 (1H, d, J=13.2 Hz, CH$_2$), 6.81 (1H, d, J=0.7 Hz, Ar—H), 7.30 (1H, t, J=6.2 Hz, Ar—H), 7.72 (1H, d, J=7.6 Hz, Ar—H), 7.78 (1H, m, Ar—H), 8.66 (1H, m. Ar—H); MS (ES$^+$) m/e 375 [MH]$^+$; Anal. Found C, 63.08, H, 4.67; N, 21.61. C$_{20}$H$_{18}$N$_6$O$_2$.0.45 H$_2$O requires C, 62.88; H, 4.98; N, 21.97%.

Example 30

3-(5-Methylisoxazol-3-yl)-6-(6-methylpridin-2-yl)methyloxy-7,8,9,10-tetrahydro-(7,10-methano)-1,2,4-triazolo[3,4-a]phthalazine 3-Chloro-6-hydrazino-4,5-diazatricyclo[6.2.1.2,7]undeca-2(7),3,5-triene was coupled with 5-methylisoxazole-3-carboxylic acid using the procedure given for Example 1, part a. The resultant triazolopyridazine was reacted with 6-methyl-2-pyridylcarbinol using the procedure given for Example 1, part b, to afford the title-compound, $^1$H NMR (360 MHz, CDCl$_3$) δ1.22–1.33 (2H, m, CH$_2$), 1.69 (1H, br d, J=9.2 Hz, CH$_2$), 1.95 (1H, br d, J=9.2 Hz, CH$_2$), 2.05–2.18 (2H, m, CH$_2$), 2.57 (3H, d, J=0.8 Hz, Me), 2.60 (3H, s, Me), 3.76 (1H, br s, CH), 4.13 (1H, br s, CH), 5.58 (2H, s, CH$_2$), 6.83 (1H, d, J=0.8 Hz, Ar—H), 7.14 (1H, d, J=7.6 Hz, Ar—H), 7.45 (1H, d, J=7.8 Hz, Ar—H), 7.64 (1H, t, J=7.8 Hz, Ar—H); MS (ES$^+$) m/e 389 [MH]$^+$.

Example 31

3-(3-Furyl)-6-(2-pyridyl)methyloxy-7,8,9,10-tetrahydro-(7,10-methano)-1,2,4-triazolo[3,4-a]phthalazine 3-Chloro-6-hydrazino-4.5-diazatricyclo[6.2.1,2,7]undeca-2(7),3,5-triene was coupled with 3-furoic acid using the procedure given for Example 1, part a. The resultant triazolopyridazine was reacted with 2-pyridylcarbinol using the procedure given for Example 1, part b, to afford the title-compound, $^1$H NMR (360 MHz, CDCl$_3$) δ1.24–1.34 (2H, m, CH$_2$), 1.68 (1H, m, CH$_2$), 1.95 (1H, m, CH$_2$), 2.04–2.20 (2H, m, CH$_2$), 3.76 (1H, br s, CH), 4.13 (1H, br s, CH), 5.60 (1H, d, J=14.2 Hz, CH$_2$), 5.64 (1H, d, J=14.0 Hz, CH$_2$), 7.25–7.30 (2H, m, 2 of Ar—H), 7.51–7.56 (2H, m, 2 of Ar—H), 7.76 (1H, m, Ar—H), 8.45 (1H, d, J=1.1 Hz, Ar—H), 8.66 (1H, m, Ar—H); MS (ES$^+$) m/e 360 [MH]$^+$; Anal. Found C, 65.04; H, 4.60; N, 18.77%. C$_{20}$H$_{17}$N$_5$O$_2$.0.6 H$_2$O requires C, 64.89; H, 4.96; N, 18.92%.

What is claimed is:

1. A compound of formula I:

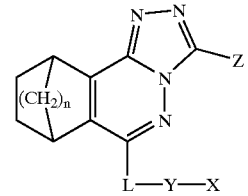

wherein:

L is O, S or NH;

X is pyridyl, optionally substituted by one or two groups independently chosen from CN, halogen, C$_{1-6}$alkyl, NR$^8$R$^9$, pyrrolidinyl, dihydropyrrolyl, pyrrolinyl, pyrrolyl, and CF$_3$ where R$^8$ and R$^9$ are each independently C$_{1-6}$alkyl, and the pyridyl is optionally in the form of the N-oxide;

Y is optionally branched C$_{1-4}$alkylidene optionally substituted by an oxo group;

Z is pyrazine, optionally substituted by a group R$^1$, NR$^2$R$^3$, azetidinyl, pyrrolidinyl, dihydropyrrolyl, pyrrolinyl, pyrrolyl, piperidinyl, trihydropyridyl, hydropyridyl, azepinyl, dihydroazepinyl, tetrahydroazepinyl, hexahydroazepinyl, NR$^2$COR$^3$, CN, CF$_3$, phenyl, benzyl or pyridyl;

R$^1$ is C$_{1-6}$alkyl, C$_{2-6}$alkenyl, C$_{2-6}$alkynyl or CF$_3$;

R$^2$ and R$^3$ are each independently hydrogen, C$_{1-6}$alkyl, C$_{2-6}$alkenyl, C$_{2-6}$alkynyl or CF$_3$; and n is 1 or 2;

or a pharmaceutically acceptable salt thereof.

2. A compound according to claim 1 of formula II:

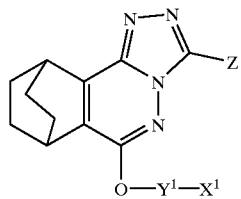

wherein

Z is defined in claim 1;

X$^1$ is pyridyl, optionally substituted by one or two C$_{1-6}$alkyl groups and optionally in the form of the N-oxide; or a pharmaceutically acceptable salt thereof.

3. A pharmaceutical composition comprising an effective amount of a compound according to claim 1 or a pharmaceutically acceptable salt thereof and a pharmaceutically acceptable carrier.

4. A compound which is:
3-(2-pyrazinyl)-6-(2-pyridyl)methyloxy-7,8,9,10-tetrahydro-(7,10-ethano)-1,2,4-triazolo[3,4-a]phthalazine; or a pharmaceutically acceptable salt thereof.

* * * * *